United States Patent [19]

Curtze et al.

[11] Patent Number: 4,933,328

[45] Date of Patent: Jun. 12, 1990

[54] PHOSPHONIUM SALTS AND FUNGICIDAL USE

[75] Inventors: Jurgen Curtze, Johannisberg, South Africa; Christo Drandarevski, Ingelheim; Guido Albert, Hackenheim, both of Fed. Rep. of Germany; Arthur A. Ramsey, Lawrenceville, N.J.

[73] Assignee: Shell Internationale Research Maatshappij B.V., The Hague, Netherlands

[21] Appl. No.: 220,736

[22] Filed: Jul. 18, 1988

[30] Foreign Application Priority Data

Jul. 18, 1987 [DE] Fed. Rep. of Germany ....... 3723913

[51] Int. Cl.$^5$ .......................... A01N 57/24; C07F 9/65
[52] U.S. Cl. ......................................... 514/92; 548/119
[58] Field of Search ........................... 548/119; 514/92

[56] References Cited

PUBLICATIONS

Krieg et al, Chemical Abstracts, vol. 95 (1981), 187133x.
Kreig et al, Liebigs Ann. Chem., 1981, pp. 623–632.

Primary Examiner—Richard L. Raymond

[57] ABSTRACT

The invention provides fungicidal compositions containing phosphonium salts of formula:

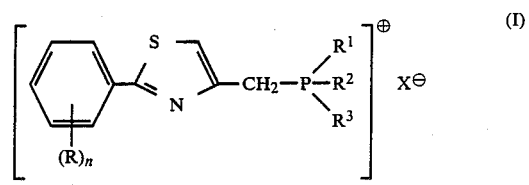

in which n represents 0, 1, 2 or 3, R represents a halogen atom or an optionally substituted alkyl, haloalkyl, alkoxy or haloalkyl group, $R^1$, $R^2$ and $R^3$ independently represent an optionally substituted alkyl, cycloalkyl, phenyl or benzyl group and X represents an anion; certain novel phosphonium salts, a process for the preparation of such compounds and a method of combating plant pathogenic fungi using such compositions or compounds.

16 Claims, No Drawings

PHOSPHONIUM SALTS AND FUNGICIDAL USE

This invention relates to fungicidal compositions containing phosphonium salts, certain novel phosphonium salts, a process for the preparation of such compounds and a method of combating plant pathogenic fungi using such compositions or compounds.

Liebigs Ann. Chem., (1981), 623-632 discloses, inter alia, 2-ethoxycarbonylthiazol-4-ylmethyl(triphenyl)-phosphonium bromide and 2-phenylthiazol-4-ylmethyl(triphenyl)phosphonium bromide. However, there is no indication in this document that either of these compounds have any fungicidal activity.

It has now been discovered that useful fungicidal activity is present in certain thiazol-4-yl phosphonium salts, some of which are novel. According to the present invention there is therefore provided a fungicidal composition which comprises at least one carrier and, as active ingredient, a compound of the general formula

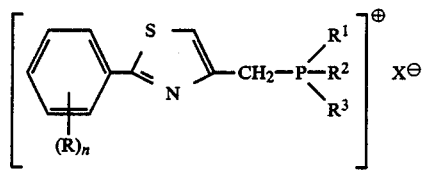

in which n represents 0, 1, 2 or 3;

R represents a halogen atom or an optionally substituted alkyl, haloalkyl, alkoxy or haloalkoxy group;

$R^1$, $R^2$ and $R^3$ independently represent an optionally substituted alkyl, cycloalkyl, phenyl or benzyl group; and X represents an anion.

When any of the aforementioned compounds contain an alkyl, haloalkyl, alkoxy or haloalkoxy substituent group, this may be linear or branched and may contain up to 12, preferably up to 6, and especially up to 4, carbon atoms.

The terms "halogen" and "halo-" encompass fluorine, chlorine, bromine and iodine, the first three, that is, fluorine, chlorine and bromine, being preferred.

When any of the foregoing substituents are designated as being optionally substituted, the substituent groups which are optionally present may be any one or more of those customarily employed in the development of pesticidal compounds, and/or the modification of such compounds to influence their structure/activity, persistence, penetration or other property. Specific examples of such substituents include for example halogen atoms, nitro, cyano, hydroxyl, alkyl, haloalkyl, alkoxy, haloalkoxy, amino, alkylamino, dialkylamino, carbonyl, alkoxycarbonyl, carboxyl, alkanoyl, alkylthio, alkylsulphinyl, alkylsulphonyl, carbamoyl, alkylamido, cycloalkyl and phenyl groups. When any of the foregoing substituents represents or contains an alkyl substituent group, this may be linear or branched and may contain up to 12, preferably up to 6, and especially up to 4, carbon atoms.

Preferably, R represents a halogen atom, a $C_{1-6}$ alkyl or haloalkyl, particularly a $C_{1-4}$ alkyl or haloalkyl, group or a $C_{1-6}$ alkoxy or haloalkoxy, particularly a $C_{1-4}$ alkoxy or haloalkoxy, group. If n represents 2 or 3, the substituents R may be the same or different.

It is preferred that $R^1$, $R^2$ and $R^3$ independently represent a benzyl group, a $C_{1-6}$ alkyl, particularly a $C_{1-4}$ alkyl, group, a $C_{3-8}$ cycloalkyl, particularly a $C_{3-6}$ cycloalkyl, group or a phenyl group optionally substituted by one or more substituents selected from halogen atoms, $C_{1-4}$ alkyl, $C_{1-4}$ haloalkyl, $C_{1-4}$ alkoxy and $C_{1-4}$ haloalkoxy groups.

Anion X is preferably derived from a strong organic or inorganic acid, halogen anions such as chlorine and bromine ions being particularly preferred.

A particularly preferred sub-group of compounds of formula I is that in which n is 0, 1 or 2; R represents a chlorine atom or a methyl, trifluoromethyl, methoxy or trifluoromethoxy group; $R^1$, $R^2$ and $R^3$ independently represent an ethyl, butyl, cyclohexyl, benzyl, phenyl, fluorophenyl, chlorophenyl, methylphenyl, trifluoromethylphenyl or methoxyphenyl group; and X represents a chlorine anion. [2-(4-chlorophenyl)-thiazol-4-ylmethyl]-triphenylphosphonium salts, that is, compounds in which n is 1, R is a chlorine atom substituted at the 4-position and $R^1$, $R^2$ and $R^3$ each represent an unsubstituted phenyl group, are especially preferred.

Many of the compounds of formula I are novel, and the invention therefore also extends to these novel compounds per se. The novel compounds are the phosphonium salts of formula I in which the substituents are as defined above, with the proviso that, when $R^1$, $R^2$ and $R^3$ each represent an unsubstituted phenyl group and n is 0 then X does not represent a bromine anion.

The invention also provides a process for the preparation of compounds of formula I, as defined above, which comprises reacting a compound of formula

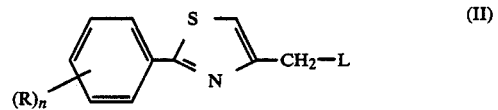

in which n and R are as defined above and L is a leaving group which may be split off as an anion, with a phosphine of formula

in which $R^1$, $R^2$ and $R^3$ are as defined above.

Preferably, leaving group L is chlorine or bromine, especially chlorine.

The reaction may be conveniently carried out in an inert solvent such as acetonitrile, acetone, toluene, dioxane or tetrahydrofuran at a temperature from 50°-150° C. On cooling, compounds of formula I can normally be separated in crystalline form.

Compounds of formula II may be prepared as follows using conventional methods:

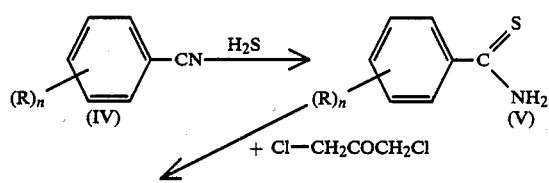

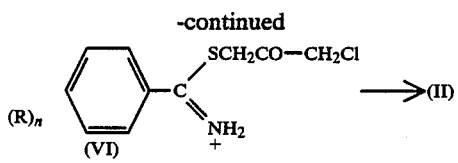

Thiobenzamides of formula V can be prepared from benzonitriles of formula IV by reacting the latter compounds with hydrogen sulphide in an organic solvent, such as toluene or pyridine, in the presence of a base, such as triethylamine, ideally at a temperature from 20°-50° C. The compounds of formula IV are either known compounds or can be prepared from known compounds by processes analogous to known processes.

Compounds of formula VI can be prepared by reacting thiobenzamides of formula V with 1,3-dichloroacetone in an inert solvent such as acetone, dioxane or toluene, preferably at a temperature from 10°-50° C. The product can be separated from the reaction medium by suction.

Dehydration of compounds of formula VI using conventional dehydration methods, such as, treatment with concentrated sulphuric acid or polyphosphoric acid, optionally with heating, produces compounds of formula II (cf. A. Silberg et al., Ber. 94, 2887-94 (1961)).

Phosphines of formula III are known compounds or can be prepared according to Houben-Weyl, Vol. 12/1, pages 17-66, published by Georg Thieme Verlag, Stuttgart 1963.

The invention also includes a method for making a fungicidal composition as defined above which comprises bringing a compound of formula I into association with at least one carrier.

A composition according to the invention preferably contains from 0.5 to 95% by weight of active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating fungicidal compositions may be used.

Suitable solid carriers include natural and synthetic clays and silcates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes, for example beeswax, paraffin wax, and chlorinated mineral waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Fungicidal compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohols or alkyl phenols, for example p-octylphenol or p-octylcresol, with ethylene oxide and/or propylene oxide; sulphates or, sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, pastes, granules, soluble powders, solutions, emulsifiable concentrates, emulsions, suspension concentrates, suspensions, and aerosols. Wettable powders usually contain 25, 50 or 75% w of active ingredient and usually contain in addition to solid inert carrier, 3-10% w of a dispersing agent and, where necessary, 0-10% w of stabiliser(s) and/or other additives such as penetrants or stickers. Dusts are usually formulated as a dust concentrate having a similar composition to that of a wettable powder but without a dispersant, and may be diluted in the field with further solid carrier to give a composition usually containing ½-10% w of active ingredient. Granules are usually prepared to have a size between 10 and 100 BS mesh (1.676-0.152 mm), and may be manufactured by agglomeration or impregnation techniques. Generally, granules will contain ½-75% w active ingredient and 0-10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 1-50% w/v active ingredient, 2-20% w/v emulsifiers and 0-20% w/v of other additives such as stabilisers, penetrants and corrosion inhibitors. Suspension concentrates are usually compounded so as to obtain a stable, non-sedimenting flowable product and usually contain 10-75% w active ingredient, 0.5-15% w of dispersing agents, 0.1-10% w of suspending agents such as protective colloids and thixotropic agents, 0-10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise'-like consistency.

Other suitable formulations include aqueous or organic solutions encapsulated in polymers, encapsulated powders and natural and synthetic materials or carriers impregnated with the active ingredient.

On account of the ionic structure of the active ingredients, particular care must be taken that the other ingredients in the formulation are compatible with the active ingredients, especially if they also have an ionic structure (e.g. dispersants such as substituted naphthalene sulphonic acid-formaldehyde condensates, lignin sulphonates, polyacrylates, phosphates and sulphates of ethoxylated fatty acids and phenols, or wetting agents such as sodium dioctyl sulphosuccinate, alkylnaphthalene sulphonates, substituted and unsubstituted fatty acid taurides and quaternary ammonium compounds). Non-ionic auxiliary substances are to be preferred.

Formulation Example

Emulsion concentrate
Composition:

| Active ingredient according to the invention | 200 g/l |
|---|---|
| Ethoxylated castor oil | 100 g/l |
| Tetrahydrofurfuryl alcohol | 793 g/l |
| Density | 1.093 g/ml |

The composition of the invention may also contain other ingredients, for example other compounds possessing herbicidal, insecticidal or fungicidal properties.

Of particular interest in enhancing the duration of the protective activity of the compounds of this invention is the use of a carrier which will provide a slow release of the fungicidal compounds into the environment of the plant which is to be protected. Such slow-release formulations could, for example, be inserted in the soil adjacent to the roots of a vine plant, or could include an adhesive component enabling them to be applied directly to the stem of a vine plant.

The invention still further provides the use as a fungicide of a compound of the general formula I as defined above or an acid-addition salt or metal salt complex thereof, and a method for combating fungus at a locus, which comprises treating the locus, which may be for example plants subject to or subjected to fungal attack, seeds of such plants or the medium in which such plants are growing or are to be grown, with such a compound.

The present invention is of wide applicability in the protection of crop plants against fungal attack. The compounds and compositions of the invention are particularly active against botrytis, especially botrytis cinerea, and may be used in all crops where botrytis attack is undesirable. Typical crops which may be protected include vines, tomatoes, strawberries, beans and ornamentals. The duration of protection is normally dependent on the individual compound selected, and also a variety of external factors, such as climate, whose impact is normally mitigated by the use of a suitable formulation.

The invention is further illustrated by the following Examples.

EXAMPLE 1

Preparation of
[2-(4-chlorophenyl)-thiazol-4-yl-methyl]-triphenylphosphonium chloride (a) 4-chlorothiobenzamide 68.8 g (0.5 mol) of 4-chlorobenzonitrile were dissolved in a mixture of 100 ml pyridine and 50 ml triethylamine. Whilst stirring, an even flow of 15 l (0.67 mol/hour) of hydrogen sulphide was introduced at room temperature, then 11 l (0.5 mol/hour) for 30 min at 50° C., i.e. a total of 1.25 mol. This was then stirred for a further 30 min at 50° C. and then mixed into 1.5 liters of water. The crystallate was drawn off, washed with plenty of water and dried, Yield: 81 g (94% of theory); m.pt. 129° C.

(b) 4-chlorothiobenzimidic acid-3-chloroacetonyl ester hydrochloride 8.58 g (50 mmol) of the 4-chlorothiobenzamide obtained in (a) were dissolved in 35 ml acetone, 6.35 g (50 mmol) of 1,3 dichloroacetone were added and left to stand for 1 day at room temperature. The crystallate was drawn off, washed with acetone and dried.

Yield: 12.2 g (82% of theory); m.pt. 149° C. (decomposition).

(c) 4-chloromethyl-2-(4-chlorophenyl)-thiazole 11.95 g (40 mmol) of the 4-chlorothiobenzimidic acid-3-chloroacetonyl ester hydrochloride obtained in (b) were introduced into 40 ml concentrated sulphuric acid at room temperature, with stirring, left to stand at room temperature for 30 minutes and then poured onto ice. The crystallate was drawn off, washed free of acid with water, and dried.

Yield: 9.6 g (98% of theory); m.pt. 81° C.

(d)
[2-(4-chlorophenyl)-thiazol-4-ylmethyl]-triphenylphosphonium chloride 2.44 g (10 mmol) of the 4-chloromethyl-2-(4-chlorophenyl)-thiazole obtained in (c), and 2.62 g (10 mmol) of triphenyl phosphine were refluxed with 20 ml of acetonitrile for 3 hours, whereupon the substance precipitated out in crystalline form. After cooling, it was drawn off and washed with acetone and then dried.

Yield: 3.65 g (72% of theory), m.pt. 308°–310° C.

EXAMPLES 2 to 34

Following procedures similar to those described in Example 1 above, further compounds according to the invention were prepared as detailed in Table I below. In this table, the compounds are identified by reference to formula I.

TABLE I

| Example No. | n | R | R¹ | R² | R³ | X | M.pt (°C.) |
|---|---|---|---|---|---|---|---|
| 2 | 0 | — | 4-CH₃O Phenyl | 4-CH₃O Phenyl | 4-CH₃O Phenyl | Cl | 203 |
| 3 | 0 | — | Phenyl | Phenyl | Phenyl | Cl | 283 |
| 4 | 2 | 3,4-(CH₃O)₂ | Phenyl | Phenyl | Phenyl | Cl | 228 (dec.) |
| 5 | 1 | 4-CF₃ | Phenyl | Phenyl | Phenyl | Cl | 294 |
| 6 | 1 | 4-CH₃ | Phenyl | Phenyl | Phenyl | Cl | 285 (dec.) |
| 7 | 1 | 2-Cl | Phenyl | Phenyl | Phenyl | Cl | 267 |
| 8 | 1 | 4-Cl | n-C₄H₉ | n-C₄H₉ | n-C₄H₉ | Cl | 143–144 |
| 9 | 1 | 4-Cl | 4-CH₃ Phenyl | 4-CH₃ Phenyl | 4-CH₃ Phenyl | Cl | 333 |
| 10 | 1 | 4-Cl | 4-CH₃O Phenyl | 4-CH₃O Phenyl | 4-CH₃O Phenyl | Cl | 230 (dec.) |
| 11 | 1 | 4-Cl | 3-Cl Phenyl | 3-Cl Phenyl | 3-Cl Phenyl | Cl | 255 |
| 12 | 1 | 4-Cl | 4-Cl Phenyl | 4-Cl Phenyl | 4-Cl Phenyl | Cl | 272 |
| 13 | 1 | 4-CH₃ | 4-CH₃ Phenyl | 4-CH₃ Phenyl | 4-CH₃ Phenyl | Cl | 302 |
| 14 | 1 | 4-CH₃ | 4-CH₃O Phenyl | 4-CH₃O Phenyl | 4-CH₃O Phenyl | Cl | 227 (dec.) |
| 15 | 1 | 4-Cl | 3-CH₃ Phenyl | 3-CH₃ Phenyl | 3-CH₃ Phenyl | Cl | 266 |
| 16 | 1 | 4-CH₃ | 3-CH₃ Phenyl | 3-CH₃ Phenyl | 3-CH₃ Phenyl | Cl | 270 |
| 17 | 1 | 4-CH₃ | 4-F Phenyl | 4-F Phenyl | 4-F Phenyl | Cl | 213 |
| 18 | 1 | 4-Cl | Cyclohexyl | Cyclohexyl | Cyclohexyl | Cl | 287 |
| 19 | 1 | 4-CH₃ | Cyclohexyl | Cyclohexyl | Cyclohexyl | Cl | 238 |
| 20 | 1 | 4-Cl | 4-F Phenyl | 4-F Phenyl | 4-F Phenyl | Cl | 240 |
| 21 | 1 | 4-CF₃ | Phenyl | Phenyl | Phenyl | Cl | |
| 22 | 1 | 4-CF₃O | Phenyl | Phenyl | Phenyl | Cl | |
| 23 | 1 | 4-Cl | Phenyl | Phenyl | n-C₄H₉ | Cl | 192 |
| 24 | 1 | 4-CH₃ | Phenyl | Phenyl | n-C₄H₉ | Cl | 119 |
| 25 | 1 | 4-Cl | 4-Cl Phenyl | 4-Cl Phenyl | n-C₄H₉ | Cl | |
| 26 | 0 | — | 4-CF₃ Phenyl | 4-CF₃ Phenyl | n-C₄H₉ | Cl | |
| 27 | 0 | — | Phenyl | Phenyl | n-C₄H₉ | Cl | |
| 28 | 1 | 4-CF₃ | Phenyl | Phenyl | n-C₄H₉ | Cl | |
| 29 | 1 | 4-CF₃O | Phenyl | Phenyl | n-C₄H₉ | Cl | |
| 30 | 1 | 4-CH₃O | Phenyl | Phenyl | n-C₄H₉ | Cl | |
| 31 | 1 | 4-Cl | Phenyl | Phenyl | C₂H₅ | Cl | 200 |
| 32 | 1 | 4-CH₃ | Phenyl | Phenyl | C₂H₅ | Cl | 174 |
| 33 | 1 | 4-CH₃ | Benzyl | Benzyl | Benzyl | Cl | 201 |
| 34 | 1 | 4-Cl | Benzyl | Benzyl | Benzyl | Cl | 210 |

EXAMPLE 35

The fungicidal activity of representative compounds of the invention was investigated by means of the following test.

Protectant activity against vine grey mould (Botrytis cinerea)

The test is a direct protectant one on the grape itself. As Botrytis cinerea normally infect grapes which have a certain sugar content, grapes are selected which have between 60 and 90 Ochsle degrees. (An Ochsle degree is a measure of the specific density of the grape juice and the sugar concentration can be calculated from this). It is also important to ensure that neither the grapes nor the stems are damaged or show any signs of necrosis.

Selected grapes are cut off about 5 mm above the start of the stem and then dipped in a solution comprising 500 ppm of the test compound in water, acetone, methanol or a mixture thereof, the solvent or solvent mixture also containing 500 ppm Triton X-100. The cut is then sealed with paraffin wax. Four controls are also set up in which grapes are treated with the following substances:

(1) H₂O = distilled water
(2) LA 0.5 = 10% acetone solution containing 500 ppm Triton X-100
(3) LM 0.5 = 10% methanol solution containing 500 ppm Triton X-100
(4) LW 0.5 = distilled water containing 500 ppm Triton X-100

The grapes are divided up according to treatment and set out in blocks on a stainless steel grid at room temperature. 30–50 grapes are used per treatment according to the homogeneity of the grape material.

After 2 days, the treated grapes are sprayed with an aqueous spore suspension of a field isolate of Botrytis cinerea containing 100 000 spores/ml using a spray gun. The grapes are then incubated in a humid room (100% relative humidity) at 20°–22° C. The infected grapes are counted at various successive times according to the development of the infection and the Abbott efficiency is then calculated as follows:

$$\text{Efficiency } E \text{ (\%)} = 100 - \sum_{i=AW_1}^{AW_n} \frac{BB_i}{K_i} \times 100$$

where
$AW_n = n^{th}$ evaluation
$AW_1 = 1^{st}$ evaluation
$BB_i = $ no of infected grapes in $i^{th}$ evaluation
$K_i = $ mean value of no. of infected grapes in all (i.e. H₂O, LA, LW and LM) controls in $i^{th}$ evaluation The results of tests carried out according to the above method are set out in the following tables. In these tables, the additional abbreviations BBx and Ex are used where x is the time in days between infection and evaluation.

TEST 1

No. of grapes = 30
No. of evaluations = 7

| Compound | Formulation | BB4 | BB5 | BB6 | BB7 | BB11 | BB12 | BB13 | E4 | E5 | E6 | E7 | E11 | E12 | E13 |
|---|---|---|---|---|---|---|---|---|---|---|---|---|---|---|---|
| H₂O Control | | 9 | 14 | 5 | 2 | 0 | 0 | 0 | 0 | 0 | 0 | 0 | 0 | 0 | 0 |
| LW Control | | 15 | 11 | 4 | 0 | 0 | 0 | 0 | 0 | 0 | 0 | 0 | 0 | 0 | 0 |

TEST 1-continued

No. of grapes = 30
No. of evaluations = 7

| Compound | Formulation | BB4 | BB5 | BB6 | BB7 | BB11 | BB12 | BB13 | E4 | E5 | E6 | E7 | E11 | E12 | E13 |
|---|---|---|---|---|---|---|---|---|---|---|---|---|---|---|---|
| LA Control | | 15 | 10 | 4 | 1 | 0 | 0 | 0 | 0 | 0 | 0 | 0 | 0 | 0 | 0 |
| LM Control | | 20 | 4 | 6 | 0 | 0 | 0 | 0 | 0 | 0 | 0 | 0 | 0 | 0 | 0 |
| Ronilan | WP 50 | 17 | 5 | 4 | 4 | 0 | 0 | 0 | −16 | 10 | 11 | 0 | 0 | 0 | 0 |
| Folpet | WP 50 | 2 | 11 | 13 | 3 | 1 | 0 | 0 | 86 | 46 | 11 | 3 | 0 | 0 | 0 |
| Benomyl | WP 50 | 30 | 0 | 0 | 0 | 0 | 0 | 0 | −104 | −23 | −3 | 0 | 0 | 0 | 0 |
| Example 1 | LM 0.5 | 1 | 3 | 19 | 4 | 3 | 0 | 0 | 93 | 83 | 21 | 10 | 0 | 0 | 0 |

TEST 2

No. of grapes = 30
No. of evaluations = 4

| Compound | Formulation | BB 3 | BB 4 | BB 5 | BB 6 | E 3 | E 4 | E 5 | E 6 |
|---|---|---|---|---|---|---|---|---|---|
| $H_2O$ Control | | 15 | 5 | 1 | 6 | 0 | 0 | 0 | 0 |
| LW Control | | 20 | 4 | 1 | 5 | 0 | 0 | 0 | 0 |
| LA Control | | 15 | 10 | 3 | 2 | 0 | 0 | 0 | 0 |
| LM Control | | 13 | 8 | 3 | 5 | 0 | 0 | 0 | 0 |
| Ronilan | WP 50 | 9 | 6 | 2 | 13 | 42 | 33 | 30 | −4 |
| Benomyl | WP 50 | 30 | 0 | 0 | 0 | −91 | −34 | −23 | −4 |
| Example 9 | LM 0.5 | 0 | 13 | 6 | 6 | 100 | 42 | 22 | 13 |
| Example 10 | LM 0.5 | 0 | 8 | 5 | 4 | 100 | 64 | 46 | 41 |
| Example 11 | LM 0.5 | 0 | 13 | 6 | 10 | 100 | 42 | 22 | 0 |
| Example 12 | LM 0.5 | 1 | 3 | 11 | 6 | 93 | 82 | 38 | 27 |
| Example 13 | LM 0.5 | 0 | 1 | 3 | 8 | 100 | 95 | 83 | 58 |
| Example 14 | LM 0.5 | 0 | 0 | 8 | 10 | 100 | 100 | 67 | 37 |

TEST 3

No. of grapes = 30
No. of evaluations = 3

| Compound | Formulation | BB 4 | BB 5 | BB 6 | E 4 | E 5 | E 6 |
|---|---|---|---|---|---|---|---|
| $H_2O$ Control | | 15 | 11 | 4 | 0 | 0 | 0 |
| LW Control | | 16 | 8 | 6 | 0 | 0 | 0 |
| LA Control | | 14 | 11 | 5 | 0 | 0 | 0 |
| LM Control | | 14 | 11 | 3 | 0 | 0 | 0 |
| Folpet | WP 50 | 5 | 21 | 4 | 66 | −4 | −2 |
| Benomyl | WP 50 | 10 | 16 | 2 | 32 | −4 | 5 |
| Example 6 | LM 1.0 | 5 | 22 | 2 | 66 | −8 | 1 |

TEST 4

No. of grapes = 30
No. of evaluations = 7

| Compound | Formulation | BB5 | BB6 | BB7 | BB10 | BB11 | BB12 | BB14 | E5 | E6 | E7 | E10 | E11 | E12 | E14 |
|---|---|---|---|---|---|---|---|---|---|---|---|---|---|---|---|
| $H_2O$ Control | | 6 | 24 | 0 | 0 | 0 | 0 | 0 | 0 | 0 | 0 | 0 | 0 | 0 | 0 |
| LW Control | | 3 | 18 | 9 | 0 | 0 | 0 | 0 | 0 | 0 | 0 | 0 | 0 | 0 | 0 |
| LA Control | | 4 | 16 | 8 | 1 | 0 | 0 | 0 | 0 | 0 | 0 | 0 | 0 | 0 | 0 |
| LM Control | | 3 | 20 | 6 | 1 | 0 | 0 | 0 | 0 | 0 | 0 | 0 | 0 | 0 | 0 |
| Ronilan | WP 50 | 0 | 20 | 10 | 0 | 0 | 0 | 0 | 100 | 14 | −3 | −1 | −1 | −1 | −1 |
| Folpet | WP 50 | 0 | 4 | 17 | 6 | 0 | 1 | 0 | 100 | 82 | 28 | 9 | 9 | 5 | 5 |
| Benomyl | WP 50 | 6 | 22 | 2 | 0 | 0 | 0 | 0 | −50 | −20 | −3 | −1 | −1 | −1 | −1 |
| Example 3 | LM 1.0 | 0 | 2 | 10 | 12 | 4 | 0 | 0 | 100 | 91 | 58 | 19 | 5 | 5 | 5 |
| Example 2 | LM 1.0 | 0 | 1 | 7 | 6 | 2 | 1 | 1 | 100 | 95 | 72 | 52 | 46 | 42 | 39 |
| Example 1 | EC 20 | 0 | 8 | 9 | 5 | 3 | 0 | 0 | 100 | 65 | 41 | 26 | 15 | 15 | 15 |

TEST 5

No. of grapes = 30
No. of evaluations = 7

| Compound | Formulation | E 4 | E 6 | E 11 | E 13 | E 18 | E 22 | E 24 |
|---|---|---|---|---|---|---|---|---|
| $H_2O$ Control | | 0 | 0 | 0 | 0 | 0 | 0 | 0 |
| LW Control | | 0 | 0 | 0 | 0 | 0 | 0 | 0 |
| LA Control | | 0 | 0 | 0 | 0 | 0 | 0 | 0 |
| LM Control | | 0 | 0 | 0 | 0 | 0 | 0 | 0 |
| Ronilan | WP 50 | −13 | −3 | −2 | 0 | 1 | −5 | −9 |
| Folpet | WP 50 | 80 | 67 | 5 | 0 | −2 | −1 | −5 |
| Benomyl | WP 50 | −22 | −19 | −10 | −7 | −6 | −5 | −5 |
| Example 15 | LM 1.0 | 100 | 91 | 81 | 77 | 63 | 60 | 53 |
| Example 16 | LM 1.0 | 100 | 87 | 77 | 74 | 56 | 56 | 49 |
| Example 19 | LM 1.0 | 100 | 95 | 69 | 70 | 34 | 20 | 20 |

TEST 6

| Compound | Formulation | No. of grapes = 30<br>No. of evaluations = 7 | | | | | | |
|---|---|---|---|---|---|---|---|---|
| | | E 16 | E 17 | E 18 | E 20 | E 23 | E 25 | E 27 |
| H₂O Control | | 0 | 0 | 0 | 0 | 0 | 0 | 0 |
| LW Control | | 0 | 0 | 0 | 0 | 0 | 0 | 0 |
| LA Control | | 0 | 0 | 0 | 0 | 0 | 0 | 0 |
| LM Control | | 0 | 0 | 0 | 0 | 0 | 0 | 0 |
| Ronilan | WP 50 | 25 | 30 | 25 | 20 | 14 | 9 | −2 |
| Benomyl | WP 50 | 50 | 40 | −4 | 1 | 2 | 4 | 4 |
| Example 1 | LM 1.0 | 100 | 100 | 85 | 44 | 42 | 32 | 32 |
| Example 17 | LM 1.0 | 100 | 10 | −56 | −42 | −38 | −36 | −36 |
| Example 18 | LM 1.0 | 100 | 100 | 100 | 75 | 77 | 77 | 77 |
| Example 20 | LM 1.0 | 50 | −20 | −41 | −48 | −43 | −41 | −47 |
| Example 23 | LM 1.0 | 75 | 30 | 3 | 1 | −3 | −2 | −2 |
| Example 24 | LM 1.0 | 100 | 50 | −26 | −30 | −20 | −19 | −19 |

We claim:

1. A compound of the general formula:

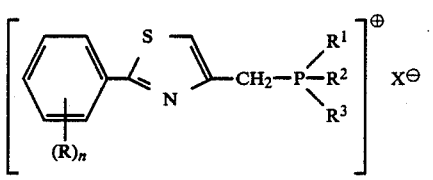

in which
n represents 0, 1, 2 or 3;
R represents a halogen atom or an optionally substituted alkyl or alkoxy group;
$R^1$, $R^2$ and $R^3$ independently represent an optionally substituted alkyl, cycloalkyl, phenyl or benzyl group; and
X represents an anion,
said optional substituents being selected from the group consisting of halogen atoms, nitro, cyano, hydroxyl, alkyl, haloalkyl, alkoxy, haloalkoxy, amino, alkylamino, dialkylamino, carbonyl, alkoxycarbonyl, carboxyl, alkanoyl, alkylthio, alkylsulphinyl, alkylsulphonyl, carbamoyl, alkylamido, cycloalkyl and phenyl groups,
with the proviso that when $R^1$, $R^2$ and $R^3$ each represent an unsubstituted phenyl group and n is 0, then X does not represent a bromine anion.

2. A fungicidal composition which comprises at least one carrier comprising a surface active agent and, as active ingredient, a compound of the general formula:

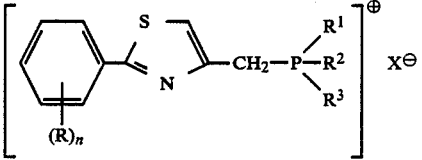

in which
n represents 0, 1, 2 or 3;
R represents a halogen atom or an optionally substituted alkyl or alkoxy group;
$R^1$, $R^2$ and $R^3$ independently represent an optionally substituted alkyl, cycloalkyl, phenyl or benzyl group; and
X represents an anion,
said optional substituents being selected from the group consisting of halogen atoms, nitro, cyano, hydroxyl, alkyl, haloalkyl, alkoxy, haloalkoxy, amino, alkylamino, dialkylamino, carbonyl, alkoxycarbonyl, carboxyl, alkanoyl, alkylthio, alkylsulphinyl, alkylsulphonyl, carbamoyl, alkylamido, cycloalkyl and phenyl groups.

3. A composition according to claim 2 in which R represents a halogen atom or a $C_{1-6}$alkyl, $C_{1-6}$haloalkyl, $C_{1-6}$alkoxy or $C_{1-6}$haloalkoxy group.

4. A composition according to claim 2 or claim 3 in which $R^1$, $R^2$ and $R^3$ independently represent a $C_{1-6}$alkyl or $C_{3-8}$cycloalkyl group or a phenyl group optionally substituted by one or more substituents selected from halogen atoms, $C_{1-4}$alkyl, $C_{1-4}$haloalkyl, $C_{1-4}$alkoxy and $C_{1-4}$haloalkoxy groups.

5. A composition according to claim 2 or claim 3 in which X represents a halogen anion.

6. A composition according to claim 2 in which n is 0, 1 or 2; R represents a chlorine atom or a methyl, trifluoromethyl, methoxy or trifluoromethoxy group; $R^1$, $R^2$ and $R^3$ independently represent an ethyl, butyl, cyclohexyl, benzyl, phenyl, fluorophenyl, chlorophenyl, methylphenyl, trifluoromethylphenyl or methoxyphenyl group; and X represents a chlorine anion.

7. A composition according to claim 2 in which n is 1, R is a chlorine atom substituted at the 4-position and $R^1$, $R^2$ and $R^3$ each represent an unsubstituted phenyl group.

8. A composition according to claim 2 which comprises at least two carriers, at least one of which is a surface-active agent.

9. A method of combating fungus at a locus which method comprises treating the locus with a fungicidally effective amount of a composition which comprises at least one carrier and, as active ingredient, a compound of the general formula:

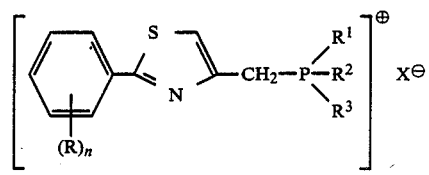

in which
n represents 0, 1, 2 or 3;
R represents a halogen atom or an optionally substituted alkyl or alkoxy group;
$R^1$, $R^2$ and $R^3$ independently represent an optionally substituted alkyl, cycloalkyl, phenyl or benzyl group; and
X represents an anion, said optional substituents being selected from the group consisting of halogen atoms, nitro, cyano, hydroxyl, alkyl, haloalkyl, alkoxy, haloalkoxy, amino, alkylamino, dialkylamino, carbonyl, alkoxycarbonyl, carboxyl, alkanoyl, alkylthio, alkylsulphinyl, alkylsulphonyl, carbamoyl, alkylamido, cycloalkyl and phenyl groups.

10. The method of claim 9 wherein R represents a halogen atom or a $C_{1-6}$ alkyl, $C_{1-6}$ haloalkyl, $C_{1-6}$ alkoxy, or $C_{1-6}$ haloalkoxy group.

11. The method of claim 9 or 10 in which $R^1$, $R^2$ and $R^3$ independently represent a $C_{1-6}$ alkyl or $C_{3-8}$ cycloalkyl group or a phenyl group optionally substituted by one or more substituents selected from halogen atoms, $C_{1-4}$ alkyl, $C_{1-4}$ haloalkyl, $C_{1-4}$ alkoxy, and $C_{1-4}$ haloalkoxy groups.

12. The method of claim 9 or 10 in which X represents a halogen atom.

13. The method of claim 9 in which n is 0, 1 or 2; R represents a chlorine atom or a methyl, trifluoromethyl, methoxy or trifluoromethoxy group; $R^1$, $R^2$ and $R^3$ independently represent an ethyl, butyl, cyclohexyl, benzyl, phenyl, fluorophenyl, chlorophenyl, methylphenyl, trifluoromethylphenyl, or methoxyphenyl group; and X represents a chlorine anion.

14. The method of claim 9 wherein n is 1, R is a chlorine atom substituted at the 4-position and $R^1$, $R^2$ and $R^3$ each represent an unsubstituted phenyl group.

15. The method of claim 9 wherein said composition comprises at least two carriers, at least one of which is a surface active agent.

16. A method according to claim 9, wherein the locus comprises plants subject to or subjected to fungal attack, seeds of such plants, or the medium in which the plants are growing or are to be grown.

* * * * *